(12) United States Patent
Witt et al.

(10) Patent No.: US 7,243,670 B2
(45) Date of Patent: Jul. 17, 2007

(54) MICROFLUIDIC SYSTEM

(75) Inventors: Klaus Witt, Keltern (DE); Monika Dittmann, Marxzell (DE); Friedrich Bek, Pfinztal (DE)

(73) Assignee: Agilent Technologies, Inc., Palo Alto, CA (US)

( * ) Notice: Subject to any disclaimer, the term of this patent is extended or adjusted under 35 U.S.C. 154(b) by 594 days.

(21) Appl. No.: 10/178,569

(22) Filed: Jun. 24, 2002

(65) Prior Publication Data

US 2003/0000835 A1 Jan. 2, 2003

(30) Foreign Application Priority Data

Jun. 28, 2001 (EP) .................... 01115587

(51) Int. Cl.
*F15C 1/04* (2006.01)
*F16K 37/00* (2006.01)

(52) U.S. Cl. .................. 137/14; 137/827; 137/828; 137/557; 204/451; 204/454; 604/201

(58) Field of Classification Search ............. 137/827, 137/828, 14; 604/201; 204/451, 454
See application file for complete search history.

(56) References Cited

U.S. PATENT DOCUMENTS

| | | | | |
|---|---|---|---|---|
| 4,908,112 A | * | 3/1990 | Pace | 210/198.2 |
| 5,599,432 A | * | 2/1997 | Manz et al. | 204/451 |
| 5,800,690 A | * | 9/1998 | Chow et al. | 204/451 |
| 5,858,195 A | * | 1/1999 | Ramsey | 204/601 |
| 5,965,001 A | | 10/1999 | Chow et al. | 204/600 |
| 6,001,231 A | * | 12/1999 | Kopf-Sill | 204/454 |
| 6,042,208 A | * | 3/2000 | Wen | 347/6 |
| 6,042,709 A | * | 3/2000 | Parce et al. | 204/453 |
| 6,156,181 A | * | 12/2000 | Parce et al. | 204/600 |

(Continued)

FOREIGN PATENT DOCUMENTS

DE 199 47 495 5/2001

(Continued)

OTHER PUBLICATIONS

Ramsey R et al., "Generating Electrospray from Microchip Devices Using Electroosmotic Pumping," Analytical Chemistry, Columbus, US, vol. 69, No. 6, Mar. 15, 1997.

*Primary Examiner*—A. Michael Chambers

(57) ABSTRACT

A microfluidic system, particularly a microfluidic chip, with at least one operational channel, in which a fluid and/or the constituents contained therein are moveable in the direction of the operational channel by a driving force, particularly by using pressure, acoustic energy, or an electrical and/or a magnetic field. At least one measurement sensor used to measure a measurable value assigned to the fluid and derivable in the region of the fluid and at least one regulator is provided to regulate the driving force and/or a parameter that may be influenced by it, wherein the regulator is coupled with a measurement sensor and a device used to alter the driving force and/or the parameter that may be influenced by it. The microfluidic system further relates to a procedure to transport and guide a fluid and/or the constituents contained therein within a microfluidic system of the type described above. For this, the regulator regulates the driving force and/or the parameter that may be influenced by it by means of a measurement sensor to measure a parameter assigned to the fluid and derivable in the vicinity of the fluid and by means of a device used to alter the driving force and/or a parameter that may be influenced by it.

11 Claims, 4 Drawing Sheets

U.S. PATENT DOCUMENTS 6,220,747 B1 * 4/2001 Gosselin ............... 366/152.3
6,221,226 B1   4/2001 Kopf-Sill ............... 204/602
6,231,737 B1 * 5/2001 Ramsey et al. ........... 204/451
6,321,791 B1 * 11/2001 Chow .................... 137/833

FOREIGN PATENT DOCUMENTS

WO  WO 01/42774  6/2001

* cited by examiner

MICROFLUIDIC SYSTEM

BACKGROUND OF THE INVENTION

1. Field of the Invention

The invention relates to a microfluidic system, particularly to a microfluidic chip, with at least one operational channel in which a fluid and/or constituents contained therein are movable in the direction of the operational channel by means of a driving force, particularly by using pressure, acoustic energy, or an electrical and/or a magnetic field, and to a procedure to transport and guide a fluid and/or constituents contained therein within such a microfluidic system.

2. Description of the Related Art

Such a device and such a procedure are already known from U.S. Pat. No. 5,965,001, U.S. Pat. No. 5,800,690, and from the journal Electrophoresis (2000), pages 100 through 106 and 107 through 115. The contents of these documents are incorporated in their entirety at this point for any purpose, since these documents disclose important features, particularly regarding the design and materials formation of such microfluidic systems and concerning possible procedures for the transport and guiding of such fluids and/or the constituents contained therein within such microfluidic systems, and thus features for which individually or in combination or in combination protection is claimed in combination with the additional features disclosed in this application, for which protection is claimed.

Such microfluidic systems are of particular interest for applications in the field of electro-osmosis and/or electrophoresis, wherein the use of an open network of miniature channels, which are mutually connected by allowing fluid communication between each other, is preferred for reasons of economy and of a correspondingly expanded application spectrum. For this, the motion of the individual fluids or cells, organisms, or constituents contained therein such as particles, ions, or neutral substances, is controlled until now mainly by exertion of electrical or electro-kinetic forces, particularly by electrical voltage, electrical current, electrical power, or other electrical parameters. These electrical parameters are usually introduced into the fluid using suitable electrodes that are in contact with so-called reservoirs at each end of the partially-crossing channels, which in turn are in fluid-connection with the individual micro-channels.

Until now, a so-called method or an "assay" has been established in expensive pre-experimentation, i.e., for a given microfluidic system, preferably a microfluidic chip, certain reagents and a certain data evaluation and also a certain temporal sequence for the electrical parameters, particularly the electrical current and/or electrical voltage at specific temperatures, are compiled as a table in a so-called "script" for each electrode. The user is eventually informed of the application area of the respective microfluidic system and of its application limits in a protocol. This protocol also specifies the limits with respect to the materials or fluids to be used and their concentrations. These limits must be defined relatively narrowly also because of the time-invariable parameters, laid out statically in the script.

Corresponding to the parameters defined in the script, the electrical parameters, particularly the electrical currents and/or the electrical voltages at the individual electrodes, are altered in stages of specified time intervals during conduction of the experiment, i.e. during the practical application of the microfluidic system, wherein special electrical circuits such as current or voltage regulators ensure that the respective electrical parameters are kept constant at the respective electrode over the desired time period.

It is understood that control of the motion of the fluids and/or the constituents contained therein becomes the more difficult the more difficult the respective microfluidic system is structured, i.e., the more mutually fluid-connected microchannels are provided. Thus, for example, in a relatively simple arrangement of four channels which are fluid-connected at one point with the formation of a cross-connection and wherein an electrode and a reservoir are provided at the ends, an independent increase in fluid flow rate between two reservoirs may be achieved not only by means of enlarging the voltage difference between two reservoirs. The voltages at the other two reservoirs must also be readjusted if the original flow rate and its direction are to be maintained. As a result, different electrical parameters are usually set at several electrodes simultaneously, i.e., according to each script. In the process the microfluidic systems are subjected to both internal and external disruptive parameter values that might strongly influence the experimental result because of the effect on any other channels present. Such disruptive parameter values may be caused, for example, by minor dimensional deviations of the microfluidic channels peculiar to their manufacture. Thus, the term "micro-fluid" pertains to miniature channels possessing a cross-section on the order of 0.1 to 500 µm. Typical dimensions of such type of miniature channels are a depth of 15 µm and a width of 40 µm, for example. The respective channel geometry determines to a great extent the effective resistance of a fluid, so that the flow rate and the electrical parameters change with an alteration of the channel geometry. Limits to the manufacturing tolerances during production of such miniature channels are however set, according to economics.

Additionally, user-specific variations caused by improper selection and preparation of fluids or substances may, for example, arise when the composition or relative salt concentration has a corresponding influence on the conductivity of the experimentation fluids and thus on the conductivity in the individual channels, which may result in a varying flow rate or migration velocity of the materials because of altered electrical parameters. Furthermore, users have shown the desire for an increased usage spectrum of such microfluidic systems, which until now could only be realized using expensive various "scripts," if at all.

Finally, it is often of great importance during quantitative determination of materials in a separation channel that the migration velocity of the fluid and/or the constituents contained therein remain essentially constant. For this, an essentially constant voltage difference must be maintained, for a specific time period, in the designated section of the separation channel provided. This also applies, for example, to a microfluidic system in which, during the separation process, a second sample substance is "pre-positioned" or "pre-injected" up to the transition point of the supply channel that is fluid-connected to the separation channel, wherein the transition point is positioned as closely as possible to the separation channel. It is also of great importance that even the slowest component of the fluid reaches the transition point within a specified time interval, certainly before the conclusion of the separation process occurring in parallel.

In both cases, additive currents in the side channels are superposed to the driving voltage in the separation channel or pre-injection channel simultaneously with the separation process or with the pre-injection process. As a result, during use of the prescribed script for performing the tests, a false testing result may occur that is dependent on internal and external disruptive parameter values.

An additional problem during the use of electro-kinetic forces with the use of electrodes is that the electrodes cannot be directly inserted into or onto the micro-channels of the microfluidic system, since undesired gas bubbles often form on the electrodes. These gas bubbles may lead to an increase in effective resistance in the miniaturized channels up to the point where the effective resistance increases without limit. For these reasons, the electrodes are usually connected with reservoirs, which can contain a relatively large fluid volume and which obviously possess larger dimensions with respect to the geometry of the miniature channels. In this manner, use of electrodes is limited to an end of the miniature channels. The electrical parameters at the intersection points or transition points at which the individual microfluidic channels terminate to one another are frequently of interest for exact and reproducible experiments.

SUMMARY OF THE INVENTION

It is therefore an object of the invention to create a microfluidic system and a procedure to transport and guide a fluid and/or the constituents contained therein such that a broader application and use spectrum and a reduced sensitivity with respect to internal and/or external disruptive parameters, and as a result a higher degree of operating reliability, are achieved.

This object is solved by the features of Patent Claim 1, particularly in that at least one measurement sensor is used to measure a measurable variable assigned or coupled to the fluid and derivable in the region of the fluid, and at least one regulator is provided to regulate the driving force and/or a parameter that may be influenced by it, wherein the regulator is coupled with a measurement sensor and with a device to alter the driving force and/or the parameter that may be influenced by it.

These measures allow the disadvantages described above to be avoided. Specifically, a better control of the particular operational behavior of individual microfluidic systems is possible, in that on internal and/or external disruptive parameter values a corresponding regulation of the driving force and/or the parameters that may be influenced by it and by the use of suitable algorithms a dynamic compliance with the nominal value, may be realized. In this manner, a broader application and usage spectrum may be achieved since the system adjusts quasi by itself, for example, for user-specific errors or for the variation of samples preferred by the user.

It is of particular advantage if at least one measurement channel feeding into the operational channel is hydrostatically connected with it and is coupled with a measurement sensor. In this manner, particularly for the channel intersections or points where one or more channels feed into one or more channels that were previously unsuitable for the use of electrodes, suitable measurement or access options for the input or output of electrical parameters may be established, in that quasi "virtual" electrodes are made available at that point. For these purposes, either a miniature channel already present at the desired location may be used, or the design of the microfluidic system may simply be altered in that an additional miniature channel is be provided, which feeds into one or more of the existing channels at the desired measurement location and which at its opposite end is fluid-connected to a suitable reservoir which, in turn, is in contact with an electrode.

The microfluidic system is advantageously designed with an open network of mutually fluid-connected channels, wherein at least three, and preferably four, of the channels feed into a common channel chamber, particularly designed point-like, wherein one of the channels functions as a measurement channel. Within the scope of such a three- or four-channel technique, material flows may be achieved that can be regulated particularly favourably or the measurement channels via the measurement channel that enable the use of economically-manipulable regulatory algorithms and enable a considerably expanded application and usage spectrum of such microfluidic systems.

In an advantageous further development of the invention, the operational channel is connected with at least two electrodes used to exert an electrical and/or magnetic field on the fluid, and wherein at least one operational electrode may be supplied with electrical current and/or electrical voltage, and wherein at least one measurement electrode serves as a measurement sensor. This configuration has proved itself particularly advantageous for fluid process regulation adjusted to the actual operational behavior during use of microfluidic systems in the field of electro-osmosis or electrophoresis.

For this, it is particularly advantageous if all electrodes may be used, or are used, both as operational electrodes and measurement electrodes. In this manner, the application and usage spectrum of existing microfluidic systems may be considerably expanded in that measurement sensors with which a favourable regulation of materials flow rate is possible, now at random channel locations that are provided with operational electrodes, are also available.

The object under discussion is also solved by a process to transport and guide a fluid and/or the constituents contained therein with in a microfluidic system, particularly a microfluidic chip, possessing at least one operational channel in which the fluid and/or the constituents contained therein are moved by a driving force, particularly by the use of pressure, acoustic energy, an electrical and/or magnetic field in the direction of the operational channel, wherein a regulator that is coupled with a measurement sensor used to measure a measurement value assigned to the fluid and derivable in the region of the fluid and with a device to alter the driving force and/or the parameter that may be influenced by it, regulates the driving force and/or the parameter that may be influenced by it.

The regulator advantageously regulates the driving force and/or the parameter that may be influenced by it in such a manner that it is/they are kept essentially particularly constant, particularly independent of internal and external disruptive parameter values so that a higher degree of operational reliability and a broader application and use spectrum are achieved. Within the scope of the disclosure of this protective right, "constant" means not only an absolute parameter value that remains the same over time, but also any parameter value function over time, or, for example, a "gradient" or a "slope" that is also invariant because of the regulation provided by the invention in reaction to internal and external disruptive parameter values.

It is of particular advantage if the regulator regulates the driving force and/or the parameter that may be influenced by it in such a manner that the gradient of the driving force and/or the gradient of the parameter influenced by the driving force is/are held essentially constant over a specified section of the operational channel, particularly independent of internal and/or external disruption values. In this manner, an essentially constant velocity or an essentially constant flow rate of the fluid or of the constituents contained therein may be achieved in the operational channel, which is of interest for many applications, particularly for those in the field of separation analysis.

It is additionally advantageous if the regulator regulates the driving force and/or the parameter that may be influenced by it in such a manner that an essentially constant or pre-determined Joulean power loss is achieved, so that the temperature of the fluid line of the operational channel is held constant, or so that the temperature increase may be determined, and as a result, be made available for further computer evaluation. For this, it is advantageous if the regulation or the identification of the sample constituents is dependent on their self-mobility in connection with the difference voltage applied to the separation channel in order to enable an identification of the sample constituents by their self-mobility with the occurrence of conductivity alterations.

It is of particular advantage if, in the microfluidic system designed as an open network of mutually fluid-connected channels, several channels feed into a common channel chamber, particularly designed point-like, wherein at least one of the channels functions as a measurement channel, and wherein the ends of the channels away from the channel chamber are in contact with an electrode used to supply an electrical field on the fluid, and wherein electrical current or electrical voltage may be supplied to the electrodes, and wherein a first electrode is assigned to a first channel and a second electrode is assigned to a second channel, characterized by the following steps:

a) Regulation of the electrical current ($I_2$) at the second electrode, functioning as a measurement sensor, to the value zero;
b) Measurement of the electrical voltage ($U_2$) at the second electrode, wherein any given voltage ($U_1$) is applied to the first electrode;
c) Regulation of the electrical voltage ($U_1$) at the first electrode in such a manner that the difference between $U_1$ and $U_2$ achieves a pre-determined value.

In this manner, such microfluidic systems may be used in applications in the field of capillary electrophoresis, fluid chromatography, and in chemical reactions, particularly for DNA/RNA-Assays or Protein-Assays, with an increased level of operational reliability with respect to internal and/or external disruptive parameter values and in a broader application and use spectrum that also satisfies current and future requirements of the applicants with consistent high quality levels of analysis results and for an extended period of time.

For this, it is further advantageous that in a microfluidic system designed as an open network of mutually fluid-connected channels, at least four channels feed into a common channel chamber, particularly designed point-like, wherein at least one of the channels functions as a measurement channel, and wherein each of the ends of at least three of the channels away from the channel chamber are in contact with an electrode, used to apply an electrical field on the fluid, and wherein electrical current or electrical voltage may be supplied to the electrodes, and wherein a first electrode is assigned to a first channel and a second electrode is assigned to a second channel and a third electrode is assigned to a third channel, characterized by the following steps:

a) Regulation of the electrical current ($I_2$) at the second electrode, which is functioning as a measurement sensor, to the value zero;
b) Measurement of the electrical voltage ($U_2$) at the second electrode, wherein any given voltage ($U_1$) is applied to the first electrode;
c) Regulation of the electrical voltage ($U_1$) at the first electrode in such a manner, that the difference between $U_1$ and $U_2$ achieves a pre-determined value;
d) Measurement of the electrical current ($I_1$) at the first electrode;
e) Calculation of the nominal current ($I_3$-nominal) at the third electrode as a sum of the current ($I_1$) measured at the first electrode and of a pre-determined current ($I_4$) assigned to the fourth channel;
f) Regulation of the electrical current ($I_3$) at the third electrode to the value of the previously-calculated nominal current ($I_3$-nominal);
g) Repetition of Steps b) through f).

In this manner, the previously-mentioned advantages may also be achieved in highly-complex microfluidic systems according to the four-channel technique and using a simple mathematical algorithm.

In accordance with an advantageous embodiment of the invention, at least two channels in a microfluidic system designed as an open network of mutually fluid-connected channels lead to a common ESI (Electro-Spray-Interface) point, wherein each of the ends of at least two of the channels away from the channel chamber are in contact with an electrode used to apply an electrical field on the fluid, and wherein electrical current and/or electrical voltage may be supplied to the electrodes, and wherein the sum of the electrical current in the overall microfluidic system is regulated so that a specific ESI residual current remains in accordance with Kirchhoff's Law.

The previously-mentioned features contribute both individually as well as in combination with one another to a microfluidic system or to a process to transport and guide a fluid and/or the constituents contained therein within such a microfluidic system that enables a broader application and use spectrum, a reduced sensitivity to internal and/or external disruptive parameter values and, as a result, a higher level of operational reliability.

BRIEF DESCRIPTION OF THE DRAWINGS

Further features, perspectives, and advantages of the invention may be taken from the following part of the description, illustrated by the Figures, in which preferred embodiment examples of the invention are described.

The Figures show.

DESCRIPTION OF THE INVENTION

Figure 1:
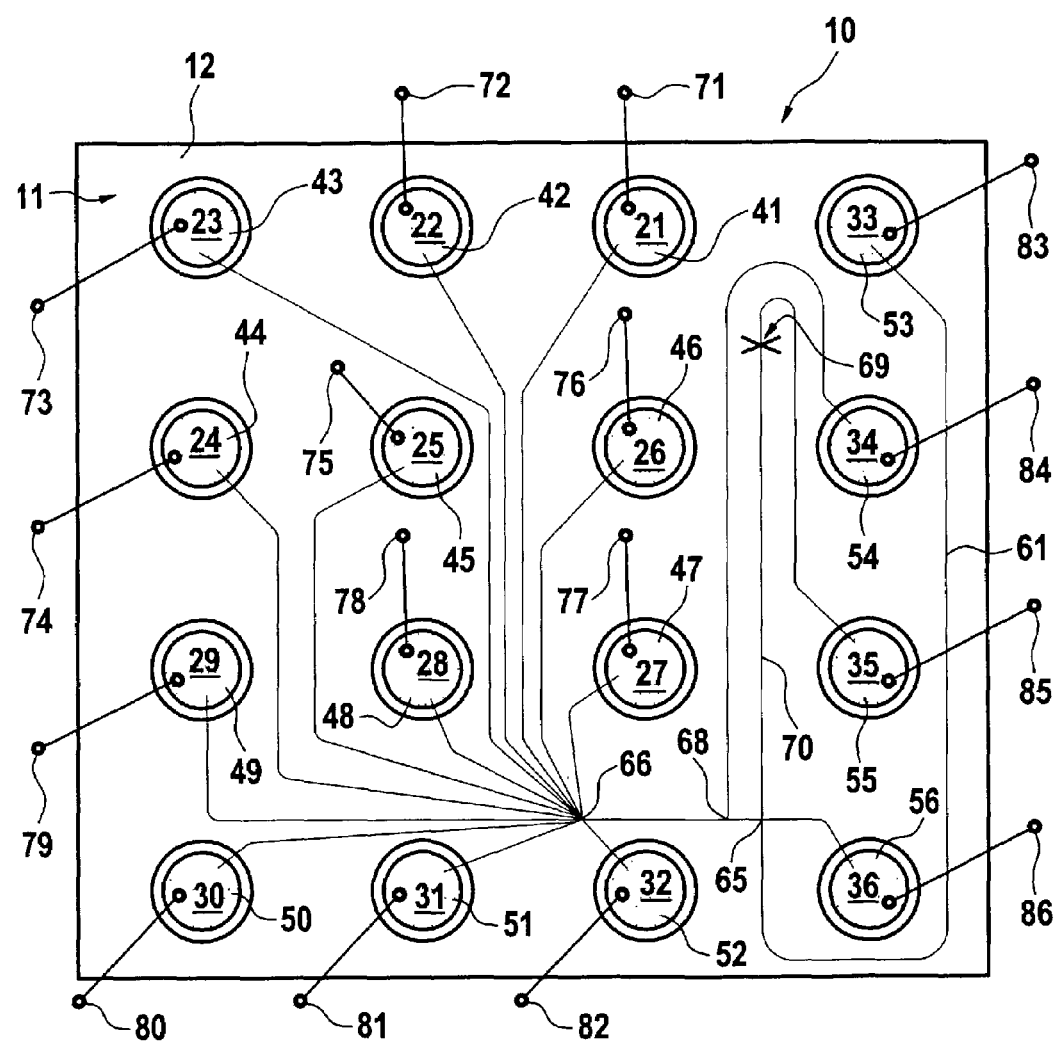
FIG. 1 a microfluidic system according to the invention in the form of a microfluidic chip with a total of sixteen reservoirs used to receive fluid substances, wherein these reservoirs are fluid-connected with an open network of micro-channels and with one separation channel serving as an operational channel that may particularly be used for electro-phoretic fluid analysis.

The microfluidic system 10 shown in FIG. 1 contains a microfluidic chip 11. It includes the substrate 12 that contains here a total of sixteen reservoirs 21 through 36 to receive diverse fluidic substances. Of these, twelve reservoirs 21 through 32 are to receive samples 41 through 52, a reservoir 33 is to receive a buffer 53 that serves as a separating medium, as well as the reservoirs 34, 35, 36 pre-filled with some buffer to receive waste 54, 55, 56. Reservoirs 21 through 36 are mutually fluid-connected via micro-channels that jointly form an open network. This means that each of the reservoirs 21 through 36 is in fluid-connection with every other reservoir. The channels that feed into reservoirs 21 through 32 also feed into a single channel in the region of a transition point 66 that then divides into two channels in the region of a transition point 68. The first of these two channels feeds into reservoir 34 that serves to receive waste 54. The second of these two channels feeds into the injection chamber of the injection point 65, which may be designed as shown, as two intersecting channels with a total of four channel sections. Channel 61 also feeds into this point. The end of this channel away from the injection chamber feeds into reservoir 33. This serves to receive the buffer 53 serving as a separating substance. The operational channel 70 feeds into the injection chamber across from the feed-in point of the channel 61. This serves to provide actual separation of the substances to be analyzed, and in turn feeds into reservoir 35 to receive the waste 55 after passing the analytical detection point 69. The injection chamber assigned to the injection point 65 is formed in the embodiment example as an intersection point of the previously-described four channel sections that are arranged in this embodiment offset at 90 degrees to one another in the same plane, wherein the opposing channel sections are arranged in alignment with each other in the case shown here.

Each reservoir 21 through 36 is in contact with one electrode 71 through 86. These electrodes serve to provide input and output of electrical voltage and/or electrical current, and may simultaneously serve as a measurement electrode according to the invention. With their help, the electrical parameters assigned to the current operational behavior of the microfluidic systems 10 can be determined and can be passed to a regulator used to regulate the driving force and/or a parameter that may be influenced by it.

In the embodiment example, electro-kinetic forces are provided as the driving force that may be introduced or transferred to the fluids 41 through 56 by the introduction or exertion of electrical voltage via electrodes 71 through 86 so that the fluids or constituents contained therein may move through the miniature channels that form an open network in accordance with the direction and velocity desired by the user.

Figure 2:
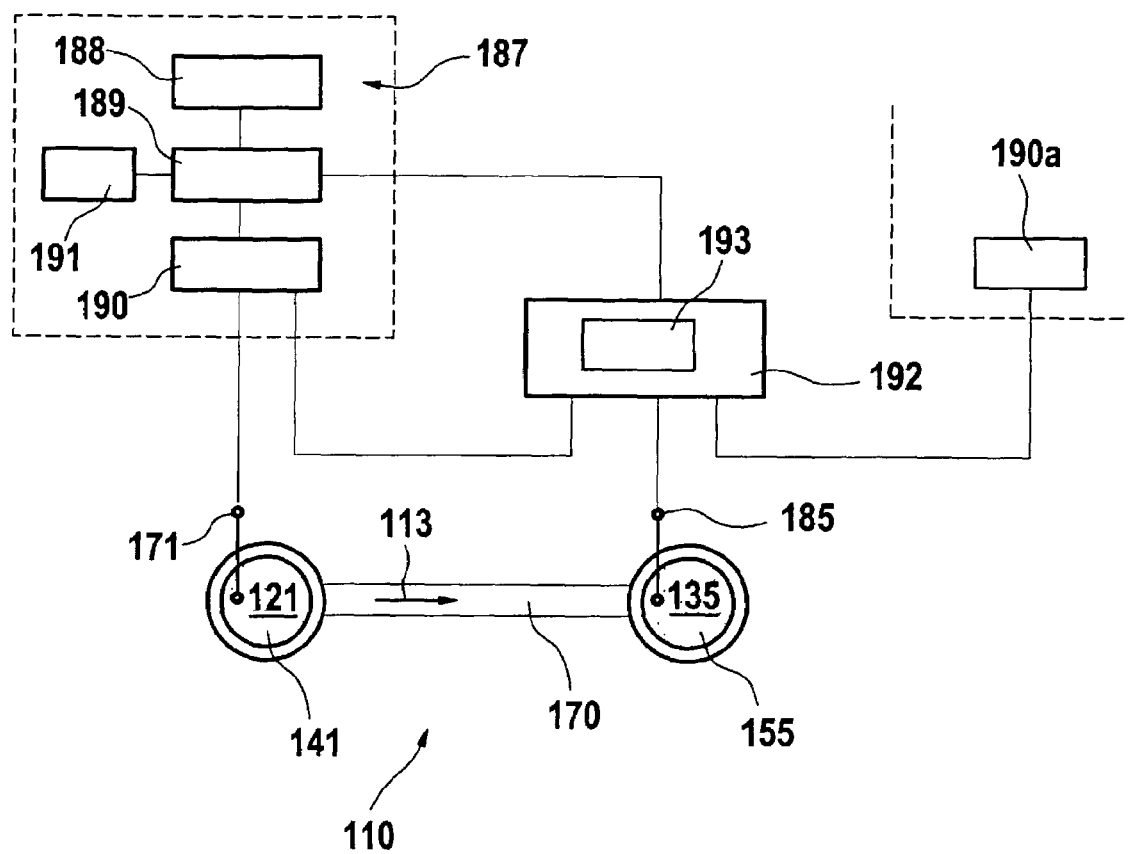
FIG. 2 a schematic representation of a simply-designed microfluidic system according to the invention, with a representation of the devices necessary for the control and regulation of electrical or electro-kinetic processes.

The microfluidic system 110 shown partially schematically in FIG. 2 is formed particularly simply. This figure also serves to show the control and regulation of the force driving the fluid or the constituents contained therein respectively and/or the parameters that may be influenced by it. The microfluidic system 110 includes the one operational channel 170 in which the fluid 141 and/or the constituents contained therein may be moved toward the operational channel 170 (arrow 113) by means of a driving force, here via an electrical or electro-kinetic field created by the voltage source 188. Reservoirs 121 and 135, which are in fluid-connection with the operational channel 170, are positioned at each of the ends of the operational channel 170.

Each reservoir 121, 135 is in contact with an electrode 171 or 185 for input or output of electrical parameter values. When an electrical voltage is applied to the electrode 171, the fluid 141 or the constituents contained therein may be moved in the direction of the operational channel 170 (arrow 113) and through it, and can subsequently reach at the other end of it, as waste 155, in reservoir 135. It is of particular importance during separation analysis in the operational channel 170, that the fluid 141 or the constituents contained therein move at an essentially constant velocity through the operational channel 170 in order to undertake the most accurate analysis possible. A characteristic parameter for the identification of a sample constituent is its self-mobility. This material constant leads to a characteristic velocity in connection with the operational parameters field strength and viscosity of the separating-medium. Since the separating-medium's viscosity is highly temperature-dependent, there is a need to exactly specify or influence the temperature assigned to the fluid in the separation channel. While the outer surface of the microfluidic chip may be brought to a desired temperature using suitable means, a higher temperature resulting from the Joulean power loss is present in the interior of the fluid that cannot be measured because of the miniaturized geometry. It is advantageous for these purposes to maintain the occurring power loss independent of internal or external disruptive influences. Reproducible operational conditions, and thus results, may thus be achieved. Dependent on the effective resistance in the operational channel and/or on the conductivity of the fluid 141 the occurring power loss may change, with the result that upon application of essentially constant voltage to electrodes 171 and 185, per the state of the art, an altered temperature with respect to the nominal value may arise that is dependent on internal and/or external disruptive parameter values in the interior of the fluid flow designated also as the fluid line, so that the instantaneous velocity of the sample constituents in the separation channel is dependent on internal and/or external disruptive parameter values via the viscosity. This may lead to correspondingly varying migration velocities of the fluid 141 and/or the constituents contained therein, so that corresponding errors in analysis, especially during identification, may occur.

In order to prevent the previously described disadvantages, the electrode 185 is provided as a measurement electrode, i.e., as a measurement sensor used to measure a parameter value (here electrical current) assigned to the fluid 141 or coupled to the fluid 141 and derivable in the region of the fluid 141. The regulator 192 is coupled (here via electrical lines) to electrode 185. This regulator 192 obeys a pre-determined mathematical algorithm 193, and may be designed as a programmable regulator. The regulator 192 for its part is coupled with a device used to alter the driving force, i.e., device 189, (which here provides electrical voltage), which forms an actuator. The device 189 is coupled with the voltage source 188 that delivers the necessary electrical voltage or electrical field. In turn, a control device 191 to control the device 189 according to pre-set parameters is connected to the device 189. This may involve parameters contained in a so-called "script" in accordance with the state of the art. These parameters may also be stored in a memory buffer such as RAM or ROM. The device 189 is further coupled with a regulator device 190 to produce stabilized, i.e., essentially constant electrical voltages or currents, that in turn are electrically coupled with the electrode 171. The regulator 192 receives the actual status from the regulator device 190 which may be converted into an actual deviation of the power loss, and thus into a correction value, with the help of the pre-determined mathematical algorithm 193 and knowledge of the current measured. This correction value is used to control the device 189 to alter the driving force. In this manner, an overlapping regulation circuit adapted to the actual operational behavior of the microfluidic system 110 may be established with which it is possible to hold essentially constant the arising power loss and thereby the temperature change in the fluid thread of the operational channel 170 independently of internal and/or external disruptive parameter values.

Identification of the sample constituents can be performed in expectation of the constant temperature behavior and with the knowledge of the measurable voltage difference at the separation channel via a time window. This time window, calculated beginning at the moment of injection, results from the corresponding mobility in the electrical field over the distance in the separation channel from the injection point to the detection point.

The voltage source 188, the device 189, the control device 191, and the regulator device 190 form the voltage supply unit 187. It is understood that such a voltage supply unit, at least the device 189 and the regulator device 190, can be employed as repeated as one likes on each or all electrodes 171, 185 and also in a microfluidic system containing more than two electrodes according to the user's needs. In such a case, the respective status of the regulation device 190a assigned to the electrode 185 may also be passed to the regulator 192.

Figure 3:
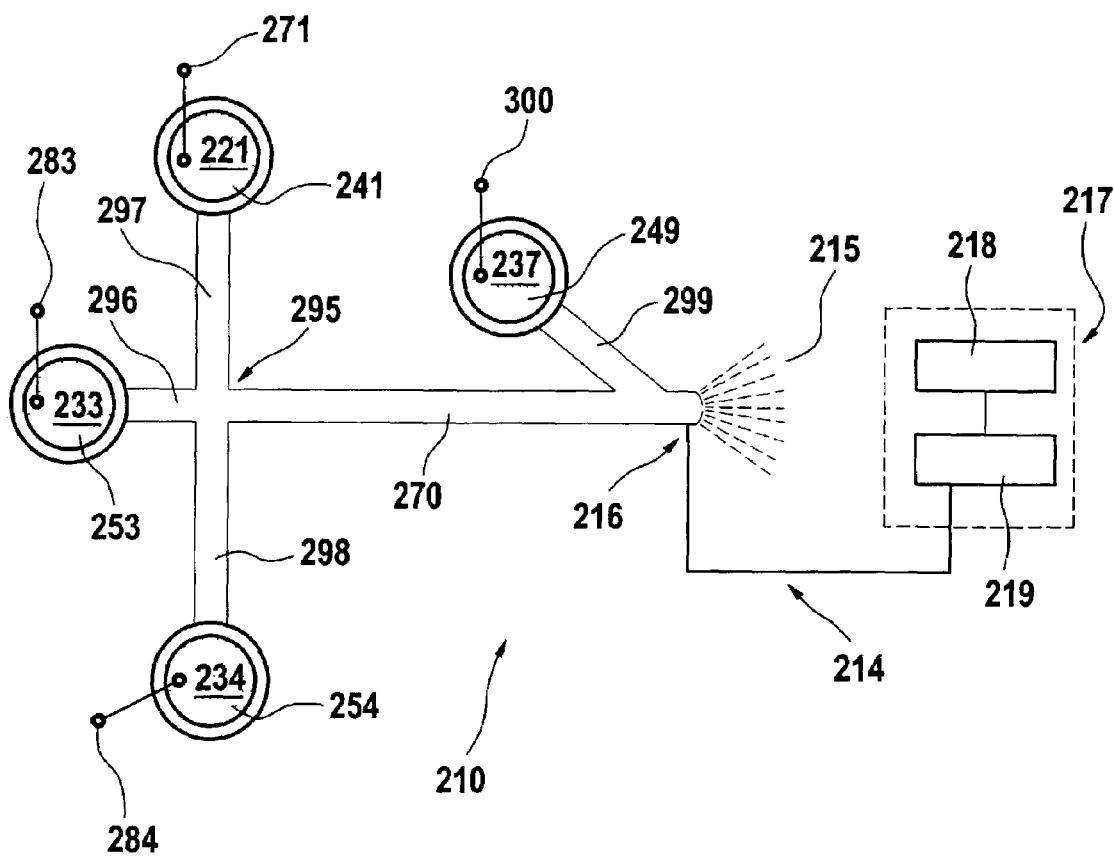
FIG. 3 another microfluidic system according to an preferred embodiment of the invention, using a reference channel and by forming a virtual electrode for the example of a mass-spectrometric analysis application.

FIG. 3 shows another microfluidic system as may be used for mass-spectroscopic analysis of fluid substances and/or the constituents contained therein. The microfluidic system 210 is formed of two channels intersecting each other at a right angle, that in turn consists of four channel sections 296, 297, 298 and 270. In the case shown here, the channel sections 296 and 270 and the channel sections 297 and 298 are respectively aligned. Further on, the channel sections 296, 297, 298 and 270 are arranged within a common plane at right angles to one another. In this, the channel sections 296, 297, 298 and 270 intersect one another at intersection point 295 that forms an injection chamber for the sample to be analyzed. There is one reservoir 233, 221 and 234 provided at each end of the channel sections 296, 297, and 298 that is in fluid-connection with the corresponding channel section. These reservoirs 221, 233 and 234 are each in contact with an electrode 271, 283, 284. In the embodiment example shown, the reservoir 221 receives the sample 241 to be analyzed, and the reservoir 234 serves to receive the waste 254. The reservoir 233 serves to receive the buffer 253 used as a separating substance. A so-called Electro-Spray-Interface (ESI) 214 is provided at the end of the channel section 270 forming the operational channel opposite the intersection point 295 or the reservoir 233. This is formed as a nozzle not shown in detail here that serves to generate the Electro-Spray 215. For the purpose of mass-spectroscopic analysis, a so-called ESI voltage is generated by means of the voltage supply 219 that serves to create the Electro-Spray 215. As a rule, the ESI voltage may be adjusted by the user in order to adapt it to a specific mass spectrometer and the prevailing conditions. For this reasons, this voltage varies from device to device or according to the prevailing conditions. The fluid flowing out at the end of the channel 270 is accelerated by means of the electrical field generated by the voltage generator 219 in the direction of the mass spectrometer's measurement sensor 218. Thus, an Electro-Spray 215 can be created which allows a mass-spectroscopic analysis of the sample to be analyzed. It is also required for this application that the voltage difference between the intersection point 295 and the nozzle end of the operational channels 270 remains essentially constant during the analysis. This, however, is not ensured by devices and procedures known to the state of the art, since the previously-described internal and/or external disruptive parameter values may lead to an alteration of the voltage difference and, accordingly, to an alteration of the electrical parameters and the flow in the operational channel.

For this purpose it could be now be anticipated to arrange a second electrode in the region of the nozzle-end of the operational channel to serve as a measurement electrode in order to allow for a regulation mechanism, in accordance with the illustration in connection with FIG. 2 or as described as follows in connection with FIG. 4. In practice, however, the use of measurement electrodes at or in the miniaturized channels is not uncritical or even impossible in many cases, because electrolytic processes and accordingly an oxidation of the electrodes may occur at the contact points, resulting in altered transition resistances. As a result of the altered transition resistances, however, electrical parameters change, and, as a result, the voltage difference varies throughout the analysis section in the separation channel. Finally, undesired bubbles may form at the contact points of the electrodes, which may unsystematically increase the effective resistance in the micro-channels having only a small flow cross-section up to the point that the effective resistance increases to an infinite value. To solve this problem, this invention presents quasi a virtual electrode 216 at the measurement point for certain electrical parameters that is of interest. It is recommended for this purpose to provide a reference channel 299 that feeds into the operational channel 270 at the measurement point of interest, and at whose opposite end is positioned a reservoir 237 to receive a measurement fluid 249 in the known manner. A measurement electrode 300 is in contact with the reservoir 237 in the known manner. It is understood that, in an embodiment of the invention particularly favourable to the above-mentioned purposes, existing channels and electrodes may be used to advantage. Thus, the disadvantages described above may be overcome by the use of such reference channels upon formation of a virtual electrode at the measurement location.

Figure 4:
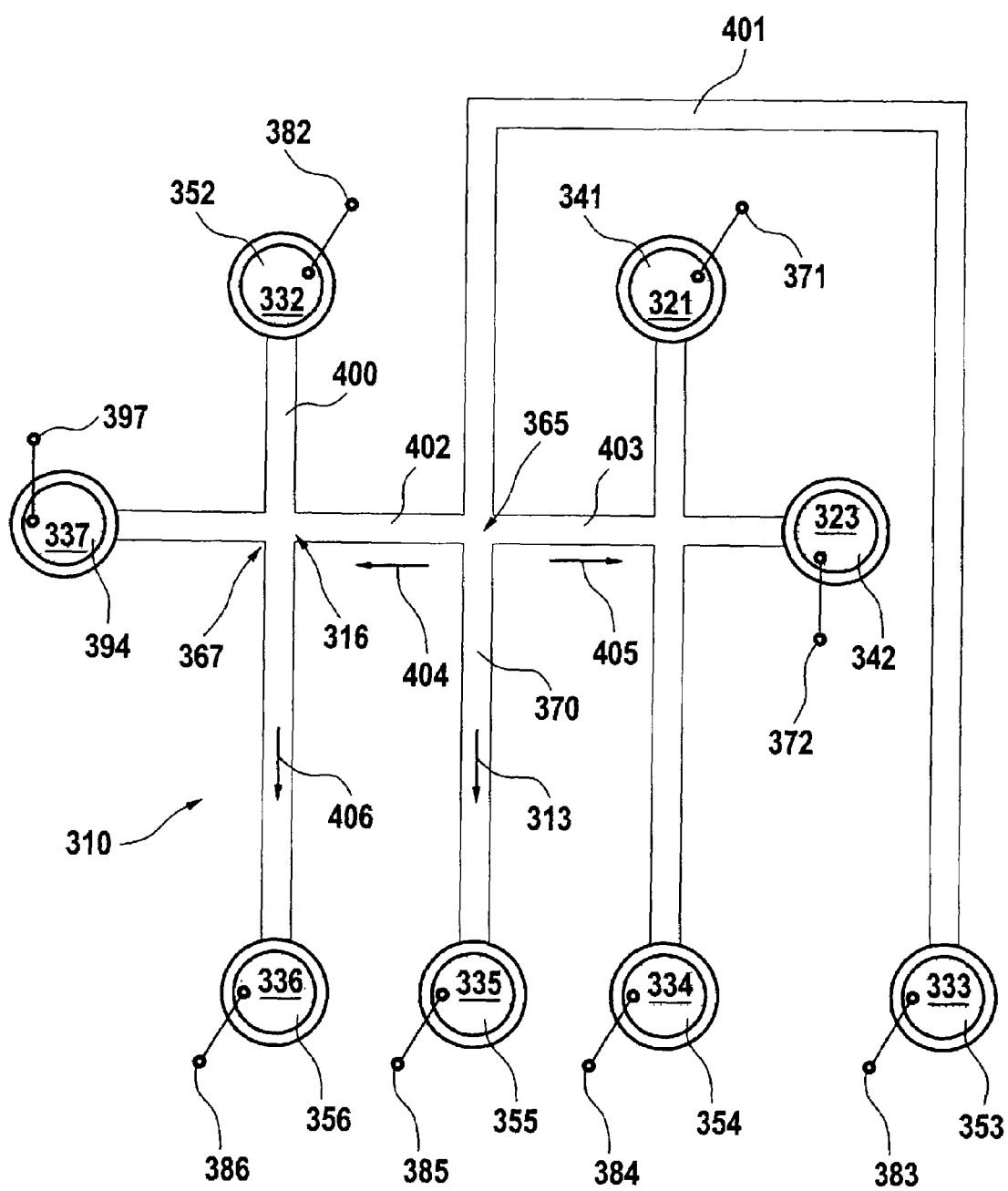
FIG. 4 another microfluidic system with a network of fluid-inter-connected micro-channels and using a reference channel in contact with a measurement electrode to elaborate a particularly advantageous procedure.

The microfluidic system 310 shown in FIG. 4 represents a partial section of the microfluidic systems 10 as shown in FIG. 1, and is also designed with channel parts similar to the microfluidic system 210 as shown in FIG. 3. The microfluidic system 310 includes a connective channel 401 that is fluid-connected with the reservoir 333 at one end into which the buffer 353 serving as a separating substance is received. This connective channel 401 feeds into an injection chamber at the injection point 365. Three other channels, namely the two side channels 402 and 403 and the operational channel 370 serving here as a separation channel, also feed into this injection chamber. The operational channel 370 includes a reservoir 335 at its end averted from the injection point 365 to receive the waste 355. The channel sections which are designed identically in the embodiment example and, in this case, symmetrically to the operational channel 370, are connected to the mutually-aligned side channels 402 and 403. For this, two channels cross at intersection points so that also four channel sections each feed into the common intersection chamber. The reservoirs 321, 332, 334 or reservoirs 332, 336, 337 are positioned to be fluid-connected with the ends of the channels other than the side channels 402 or 403 that feed into the intersection chambers. Each reservoir 321, 332, 332, 333, 334, 335, 336, 337 is in contact with one electrode 371, 372, 382, 383, 384, 385, 386, 397 each that serves for the input or output of electrical parameters, particularly electrical voltage and/or electrical current. The samples 341, 342, and 352 are in the reservoirs 321, 332, and 332, and reservoir 337 contains in this case the reference fluid 394. It is understood that the reservoir 337 is in general also useable to receive a sample fluid.

In the following, another important embodiment example of the procedure according to the invention is explained. A major advantage of microfluidic systems formed as an open network with mutually fluid-connected channels, particularly of microfluidic chips, is the fact that they enable particularly economical operation with a large number of various samples in a small space. It is therefore normal during electro-phoretic and/or electro-osmotic separating analyses that in parallel with separating analysis of a specific sample substance, e.g. sample 341, to prepare the next operational step or the subsequent separating analysis in such a manner, that the next sample in a so-called pre-injection phase, e.g., sample 352, is "drawn along" to the injection point 365 positioned as closely as possible to the transition point 367. It is absolutely necessary for a defined temporal progression of this pre-injection phase that all sample constituents of the next sample 352 progress to the transition point 367. Otherwise, not all sample constituents would be available in the separation channel 370 for the subsequent analysis. As a result, a constant voltage difference must be adjusted in the channel section reaching the transition point 367 and with its other end in the reservoir 332 serving to receive the next sample 352 in order to assume an anticipated movement distance after the elapse of a certain time interval. Accordingly, this channel section is also formed as an operational channel 400. In this manner, it may be ensured that all sample constituents in the original concentration are traveled to the transition point 367 within a specified time interval so that, during subsequent switching of the individual electrodes, the sample may be guided through the side channel 402 into side channel 403 so that another injection procedure by application of voltage to the electrode 383, and injection of buffer solution 353 through connective channel 401 caused thereby, is subsequently possible.

In order to ensure a correspondingly reliable pre-injection phase without allowing corrosion or other electrolytic-caused consequences at the transition point 367 of interest, a reference channel is provided at whose end averted from the transition point 367 the reservoir 337 with the reference fluid 394 or another sample is positioned. In this manner, a type of virtual electrode may be created at the transition point 367. This is achieved by setting firstly the electrical current ($I_2$) at the second electrode 397 functioning as a measurement sensor to the value zero so that the electrical voltage ($U_2$) at the second electrode 397 may be measured or determined in this manner. For this, any particular voltage ($U_1$) is applied to the first electrode 382 that is in contact with the reservoir 332 receiving the sample 352.

Next, the electrical voltage ($U_1$) at the first electrode 382 is regulated to an increased voltage value which is increased by a pre-determined voltage value, e.g. 200 volts. For this, the voltage difference that has proved useful or necessary for the movement of the respective fluid or of the constituents contained therein in pre-experiments in the time provided is selected as the pre-determined voltage value. If electrical parameters in the operational channel 400 change because of internal or external disruptive parameter values, the desired voltage difference may be held essentially constant by means of the regulator according to the invention corresponding to the embodiment example taken from FIG. 2, by again measuring the electrical voltage ($U_2$) at the second electrode 397 formed as a measurement electrode, and by proceeding according to the steps described above.

Because of the open hydraulic connection of the individual channels with one another, it is necessary during parallel separating analysis in the separating and operational channel 370 that specific electrical compensating currents 404 or 405 leading away from the injection point 365 in the direction of the side channels 402 and 403 are adjusted. For this purpose, the procedure described above may be advantageously expanded in such a manner that also the electrical current ($I_1$) at the first electrode 382 is measured, and then a nominal current ($I_3$-nominal) at the third electrode 386 is calculated by the use of a suitable algorithm, which in the embodiment example involves the application of Kirchhoff's Law, according to which the sum of all currents always equals zero, and thus is constant. As a result, the nominal current ($I_3$-nominal) at the third electrode 386 is calculated as the sum of the current ($I_1$) measured at the first electrode 382 and a pre-determined or pre-determinable current ($I_4$) (arrow 404) in the side channel 402 also designated as the fourth channel. Then the current ($I_3$) at the third electrode 386 is regulated to the value of the previously-calculated nominal current ($I_3$-nominal) by means of an additional regulation device not shown in detail in the Figures. In the latter case, the first electrode 382 as a result also serves as a measurement electrode used to measure the electrical current ($I_1$).

In the manner described above, by repetition of the respective steps using suitable regulation devices, it may be attained as a result that independent of internal and/or external disruptive parameter values both the differential voltage over the section between the contact area of the first electrode 382 and the transition point 367 of the operational channel 400 for the pre-injection phase, may be set to an essentially constant voltage and an essentially constant, pre-determined current $I_4$ (compensatory current 404) may be set in the side channel 402 that connects the transition point 367 with the injection point 365 necessary to allow performance of the separation process running in parallel to the pre-injection phase in the desired manner.

The invention claimed is:

1. A method to transport a substance within a microfluidic system having an operational channel in which the substance is moved by a driving force in a direction of the operational channel, wherein the method comprises:

applying the driving force;

measuring a variable assigned to the substance and derivable in an area of the substance; and regulating the driving force based on the measured variable, wherein the microfluidic system is configured as an open network of mutually fluid-connected channels that feed into a common channel chamber, wherein at least one of the channels functions as a measurement channel, wherein each of the ends of the channels away from the common chamber is in contact with an electrode that is used to exert an electrical field on the fluid, wherein the electrodes are supplied with an electrical force, wherein a first electrode is assigned to a first channel and a second electrode is assigned to a second channel, and wherein said method further comprises:

regulating an electrical current ($I_2$) to a target value at the second electrode, wherein the second electrode functions as a measurement sensor;

measuring an electrical voltage ($U_2$) at the second electrode, wherein a voltage ($U_1$) is applied to the first electrode; and regulating the electrical voltage ($U_1$) at the first electrode in such a manner that a difference between $U_1$ and $U_2$ achieves a pre-determined value.

2. A method to transport a substance within a microfluidic system having an operational channel in which the substance is moved by a driving force in a direction of the operational channel, wherein the method comprises:

applying the driving force;

measuring a variable assigned to the substance and derivable in an area of the substance; and regulating the driving force based on the measured variable, wherein the microfluidic system is configured so that at least four channels feed into a common channel chamber, wherein at least one of the channels functions as a measurement channel, wherein each of the ends of at least three channels away from the common chamber is in contact with an electrode that is used to exert an electrical field on the substance, wherein the electrodes may be supplied with an electrical force, wherein a first electrode is assigned to a first channel, a second electrode is assigned to a second channel, and a third electrode is assigned to a third channel, and wherein said method further comprises:

regulating an electrical current ($I_2$) to a target value at the second electrode, wherein the second electrode functions as a measurement sensor;

measuring an electrical voltage ($U_2$) at the second electrode, wherein a voltage ($U_1$) is applied to the first electrode;

regulating the electrical voltage ($U_1$) at the first electrode in such a manner that the difference between $U_1$ and $U_2$ achieves a pre-determined value;

measuring an electrical current ($I_1$) at the first electrode;

calculating a nominal current ($I_3$-nominal) at the third electrode as a sum of the current ($I_1$) measured at the first electrode and a predetermined current ($I_4$) assigned to the fourth channel;

regulating the current ($I_3$) at the third electrode to the value of the previously-calculated nominal current ($I_3$-nominal); and repeating the aforementioned steps.

3. A method to transport a substance within a microfluidic system having an operational channel in which the substance is moved by a driving force in a direction of the operational channel, wherein the method comprises:

applying the driving force;

measuring a variable assigned to the substance and derivable in an area of the substance; and regulating the driving force based on the measured variable, wherein the microfluidic system is configured so that at least two channels feed into a common electro-spray-interface (ESI) point, wherein each of the ends of at least two channels away from the common chamber is in contact with an electrode that is used to exert an electrical field on the fluid, and wherein said method further comprises:

regulating a sum of electrical current in the microfluidic system in such a manner that a specific residual ESI current remains.

4. A microfluidic system comprising:

a first channel that holds a first portion of a substance;

a second channel that holds a second portion of said substance;

an intersection of said first and second channels;

a source of a force;

an electrode in contact with said second channel, wherein said electrode introduces said force into said second channel to move said second portion of said substance through said second channel; and a processor that:
  (a) receives a first value of a parameter for said substance at a point in said first channel; and
  (b) determines a second value of a parameter for said substance at said intersection, based on said first value.

5. The microfluidic system of claim 4, further comprising:

a sensor that measures said parameter at said point and provides said first value.

6. The microfluidic system of claim 4, further comprising:

a third channel, wherein said first, second and third channels feed into a common channel chamber, and wherein said first channel functions as a measurement channel.

7. The microfluidic system of claim 4, wherein said parameter for said substance at said point in said first channel, and said parameter for said substance at said intersection, are of same units of measure.

8. The microfluidic system of claim 4, wherein said parameter for said substance at said point in said first channel, and said parameter for said substance at said intersection, are different units of measure from one another.

9. The microfluidic system of claim 4, wherein said parameter for said substance at said point in said first channel is selected from the group consisting of: voltage, electrical current, velocity of said substance, temperature, pressure, and acoustic energy.

10. The microfluidic system of claim 4, wherein said first value is indicative of said force being applied to said second portion of said substance, and wherein said processor also controls said source to adjust said force to attain a desired value for said second value.

11. A microfluidic system comprising:

a first channel that holds a first portion of a substance;

a second channel that holds a second portion of said substance;

an intersection of said first and second channels;

a source of a force;

an electrode in contact with said second channel, wherein said electrode is controllable to either (a) introduce said force into said second channel, or (b) measure a parameter at a first point in said second channel; and a processor that:
  (a) receives a first value of a parameter for said substance at a point in said first channel; and
  (b) determines a second value of a parameter for said substance at said intersection, based on said first value.

* * * * *